United States Patent [19]

Mazur

[11] 4,012,367

[45] Mar. 15, 1977

[54] ANTI-ULCER POLYPEPTIDES CONTAINING L-ASPARTIC ACID AND INTERMEDIATES THERETO

[75] Inventor: Robert H. Mazur, Deerfield, Ill.

[73] Assignee: G. D. Searle & Co., Chicago, Ill.

[22] Filed: Feb. 5, 1976

[21] Appl. No.: 655,338

[52] U.S. Cl. .................. 260/112.5 R; 424/177
[51] Int. Cl.$^2$ .............. C07C 103/52; A61K 37/00
[58] Field of Search ...................... 260/112.5 R

[56] References Cited

UNITED STATES PATENTS 3,896,103  7/1975  Hardy et al. .............. 260/112.5 R

*Primary Examiner*—Lewis Gotts
*Assistant Examiner*—Reginald J. Suyat
*Attorney, Agent, or Firm*—Barbara L. Cowley; John J. McDonnell

[57] ABSTRACT

This invention encompasses novel tetrapeptide amides and their intermediates containing an L-aspartic acid residue. These peptides are inhibitors of gastric acid secretion and therefore useful in the treatment of ulcers.

11 Claims, No Drawings

ANTI-ULCER POLYPEPTIDES CONTAINING L-ASPARTIC ACID AND INTERMEDIATES THERETO

The present invention is concerned with tetrapeptide amides characterized by an L-aspartic acid residue. More particularly, this invention is concerned with compounds of the formula

wherein
A is hydrogen, alkanoyl containing 2 to 6 carbon atoms, succinyl, t-butoxycarbonyl, benzyloxycarbonyl, D-pyroglutamyl or L-pyroglutamyl;
W is Trp or D-Trp;
X is Met, D-Met, Nle or D-Nle;
Y is a radical of the formula

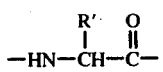

wherein R' is an alkyl radical containing 1 to 6 carbon atoms or an alkyl(cycloalkyl)radical containing 6 or 7 carbon atoms and the stereochemical configuration is D, or Y is a radical of the formula

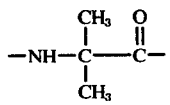

and R is hydrogen or an alkyl radical containing 1 to 6 carbon atoms; wherein the optically active amino acid residues are of the L-configuration unless otherwise indicated; and intermediates thereto.

Particularly preferred compounds of this invention are those of the formula

wherein A is hydrogen or t-butoxycarbonyl; Y is a radical of the formula

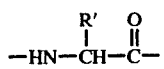

wherein R' is an alkyl radical containing 1 to 6 carbon atoms or a methylcyclopentyl radical and the stereochemical configuration is D, or Y is a radical of the formula

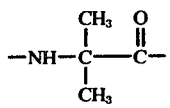

and R is hydrogen or an alkyl radical containing 1 to 6 carbon atoms; and the optically active amino acid Trp, Met and Asp residues are of the L-configuration.

The alkyl groups referred to above contain 1 to 6 carbon atoms and are exemplified by methyl, ethyl, propyl, isopropyl and the like.

Equivalent to the enformulated compounds for the purposes of this invention are solvates thereof in which biologically insignificant amounts of solvent are present.

Equivalent to the compounds of formula (I) for the purposes of this invention are the pharmaceutically acceptable acid addition salts thereof. Such acid addition salts can be derived from a variety of inorganic and organic acids such as sulfuric, phosphoric, hydrochloric, hydrobromic, hydriodic, nitric, sulfamic, citric, lactic, pyruvic, oxalic, maleic, succinic, tartaric, cinnamic, acetic, trifluoroacetic, benzoic, salicyclic, gluconic, ascorbic and related acids.

Abbreviations connote the amino acids defined in accordance with the nomenclature rules published by the IUPACIUB Commission on Biochemical Nomenclature in Biochem. J., 126, 773–780 (1972). The amino acids have the L-stereochemical configuration unless otherwise indicated.

The compounds of the present invention are useful in consequence of their valuable pharmacological properties. They are, for example, gastric anti-secretory agents as evidenced by their ability to inhibit the gastric acid secretion induced by the administration of pentagastrin.

The assay utilized for detection of that property is a modification of the procedure described by Ghosh and Schild, J. Physiol., Lond., 128:35–36P (1955); Br. J. Pharmacol. Chemother., 1300:54–61 (1958); and by Smith et al., Br. J. Pharmacol., 38:206–213 (1970). The details of that assay are as follows:

A group of male Charles River rats weighing 300–400 g. are anesthetized by the intramuscular administration of urethane at a dose of 1.5 g./kg. The trachea is exposed and cannulated and a polyethylene tube is passed through the esophagus into the cardiac junction of the stomach and is ligated in place in the neck, excluding the vagal nerves. The external jugular vein is exposed and cannulated to facilitate intravenous administration. The femoral artery is exposed and cannulated for recording of blood pressure. The abdomen is opened. A small glass cannula is passed through an incision in the duodenum gently into the stomach and secured by tying a ligature around the pyloric sphincter. A small longitudinal incision is made in the stomach, parallel to the greater curvature. The interior of the stomach is washed with warm saline until all food is evacuated. The incision is then closed with a continuous suture and the stomach is returned into the abdominal cavity. The body temperature is maintained at 30° C. by a rectal contact thermometer operating a 100 watt lamp placed over the animal. The stomach is continuously perfused through the esophageal cannula with 1/4,000 N sodium hydroxide solution flowing at the rate of 1–2 ml./min. to maintain gastric effluent pH from the pyloric cannula at a value of 6.0 to 6.5. A direct recording pH meter is connected to the physiograph for the measurement of gastric pH. Pentagastrin, a stimulant of gastric acid secretion, is administered intravenously at a standard dose of 0.1 mcg./rat. The test compounds are evaluated for their ability to antagonize the secretory response induced by the administration of pentagastrin. A test compound is considered active if the standard pentagastrin response is blocked to the extent of at least 50%.

A representative compound of the present invention which is rated as active in this assay is N-t-butoxycarbonyl-L-tryptophanyl-L-methionyl-L-aspartyl-D-alanine amide.

The compounds of formula (I) may be combined with various typical pharmaceutical carriers to provide compositions suitable for use in the treatment of gastric and/or duodenal ulcers. The dosage of these compounds is dependent upon various factors, such as the particular compound employed and the patient's individual response. Typical dosages for use as an anti-ulcer agent vary from 10 μg to 1 mg./kg. per day administered parenterally.

Additionally, the novel tripeptide amide intermediates of the formula

A—X—Asp—Y—NH$_2$ (III)

wherein A is hydrogen, alkanoyl containing 2 to 6 carbon atoms, succinyl, t-butoxycarbonyl, benzyloxycarbonyl, D-pyroglutamyl or L-pyroglutamyl;

X is Met, D-Met, Nle or D-Leu;
Y is a radical of the formula

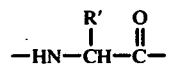

wherein R' is an alkyl radical containing 1 to 6 carbon atoms or an alkyl(cycloalkyl)radical containing 6 to 7 carbon atoms and the stereochemical configuration is D, or Y is a radical of the formula

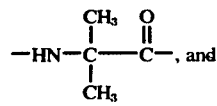

R is hydrogen or an alkyl radical containing 1 to 6 carbon atoms; are inhibitors of gastric-acid secretion when tested in the aforementioned assay. A particularly active tripeptide amide when tested in this assay is N-t-butoxycarbonyl-L-methionyl-L-aspartyl-D-alanine amide.

The manufacture of the instant novel compounds is conveniently achieved by processes adapted to the synthesis of peptides. Thus, the C-terminal amide, optionally substituted, is coupled with an active ester of an appropriately N-protected L-α-aspartic and β-carboxy protected acid to afford the corresponding N-protected dipeptide amide. Removal of the N-protecting and β-carboxy-protecting groups is followed, similarly, by coupling with the active ester of the N-protected amino acid required to produce the desired tripeptide amide. The N-protecting group is again removed and the tripeptide amide coupled with the active ester of the N-protected amino acid to afford a N-protected tetrapeptide amide. Optional removal of the N-protecting group affords, as a product, the tetrapeptide amide. As a specific example, D-alanine amide is coupled with N-benzyloxycarbonyl-L-aspartic acid α-2,4,5-trichlorophenyl, β-benzyl diester; the resulting β-benzyl-N-t-butoxycarbonyl-L-α-aspartyl-D-alanine amide is hydrogenated in aqueous acetic acid with palladium metal catalyst to produce L-aspartyl-D-alanine amide. This product is then contacted with N-t-butoxycarbonyl-L-methionyl2,4,5,trichlorophenyl ester to afford N-t-butoxycarbonyl-L-methionyl-L-aspartyl-D-alanine amide, which, after removal of the N-protecting group, is reacted with N-t-butoxycarbonyl-L-tryptophanyl-2,4,5-trichlorophenyl ester to give the N-t-butoxycarbonyl-L-tryptophanyl-L-methionyl-L-aspartyl-D-alanine amide. Optionally, the t-butoxycarbonyl protecting group may then be removed to afford L-tryptophanyl-L-methionyl-L-aspartyl-D-alanine amide.

The aforementioned procedures are preferably carried out in accordance with standard organic chemical techniques, whereby each intermediate peptide amide is produced as described hereinbefore and isolated prior to coupling with the next appropriate N-protected amino acid active ester.

Suitable active esters are those which cause the acid function of the amino acid to become more reactive such as alkyl esters with electron withdrawing (negative) substituents, vinyl esters, enol esters, phenyl esters, thiophenyl esters, nitrophenyl esters, 2,4-dinitrophenyl esters, trichlorophenyl esters, and nitrophenylthiol esters. The use of 2,4,5-trichlorophenyl esters is particularly preferred for the preparation of the present compounds.

The amino functions of the intermediates of this invention may be protected by commonly used amino protecting groups such as aryl-lower alkyl groups, such as diphenylmethyl or triphenylmethyl groups, which are optionally substituted by halogen, nitro, lower alkyl or lower alkoxy, for example; benzhydryl, trityl, and di-paramethoxybenzhydryl; acyl groups, such as formyl, trifluoroacetyl, phthaloyl, p-toluenesulphonyl, benzenesulphonyl, benzenesulphenyl and o-nitrophenylsulphenyl; groups derived from carbonic acid or thiocarbonic acid, such as carbobenzoxy groups which are optionally substituted in the aromatic radical by halogen atoms, nitro groups or lower alkyl, lower alkoxy or lower carbalkoxy groups, for example, carbobenzoxy, p-bromocarbobenzoxy or p-chlorocarbobenzoxy, p-nitrocarbobenzoxy and p-methoxycarbobenzoxy; coloured benzyloxycarbonyl groups such as p-phenylazobenzyloxycarbonyl and p-(p'-methoxyphenylazo)benzyloxycarbonyl, tolyloxycarbonyl, 2-phenyl-2-propoxycarbonyl, 2-tolyl-2-propoxycarbonyl and 2-(parabiphenylyl)-2-propoxycarbonyl; and aliphatic oxycarbonyl groups, such as t-butoxycarbonyl, allyloxycarbonyl, cyclopentyloxycarbonyl, t-amyloxycarbonyl. A particularly preferred N-protecting group for use in this invention is the t-butoxycarbonyl group.

The amino groups can also be protected by forming enamines, obtained by reaction of the amino group with 1,3-diketones, for example benzoylacetone, or acetylacetone.

Protecting groups are conveniently removed by reactions such as reduction with sodium in liquid ammonium, hydrogenolysis (for instance, in the presence of a palladium black catalyst), treatment with a hydrohalo acid (such as hydrobromic, hydrofluoric or hydrochloric acids) in acetic acid, or treatment with trifluoroacetic acid.

The following examples describe in detail the preparation of compounds illustrative of the present invention. It will be apparent to those skilled in the art that many modifications, both of materials and methods, may be practiced without departing from the purpose and intent of this disclosure. Throughout the examples hereinafter set forth, temperatures are given in degrees Centigrade (°C.) and relative amounts in parts by weight, except as otherwise noted.

EXAMPLE 1

To 787 parts of methanol is added dropwise, with stirring, 62.3 parts of thionyl chloride. Then 37.43 parts of D-alanine is added, and the mixture heated to reflux. After refluxing for 24 hours, the mixture is cooled and stripped to a low volume under reduced pressure. Trituration with ethyl ether affords D-alanine methyl ester hydrochloride, melting at about 99°–103° C.

58.0 Parts of D-alanine methyl ester hydrochloride is shaken with 83 parts by volume of a 5 M potassium carbonate solution. The resulting mixture is then extracted three times with portions of methylene chloride. The methylene chloride extracts are combined, dried over anhydrous magnesium sulfate, and stripped to a low volume under reduced pressure. The oily residue is dissolved in a solution of 310 parts of methanol and 200 parts by volume of liquid ammonia and allowed to stand at room temperature for 24 hours. Removal of the solvent under reduced pressure affords an oil, which upon trituration with ethyl ether and cooling, crystallizes. The crystalline material is filtered, dried under vacuum, and recrystallized from isopropyl acetate, to afford D-alanine amide, melting at about 75°–80° C.

EXAMPLE 2

To a solution of 18.3 parts of D-alanine amide in 355 parts of tetrahydrofuran and 157 parts acetonitrile is added 111.9 parts of N-benzyloxycarbonyl-L-aspartic acid α-2,4,5-trichlorophenyl, β-benzyl diester with stirring. After stirring for about 5 minutes the mixture solidifies and is then allowed to stand at room temperature for about 72 hours. The reaction mixture is then cooled, filtered, and washed with cold ethyl ether to afford β-benzyl-N-benzyloxy-carbonyl-L-aspartyl-D-alanine amide melting at about 173.5°–175° C. and represented by the following structural formula.

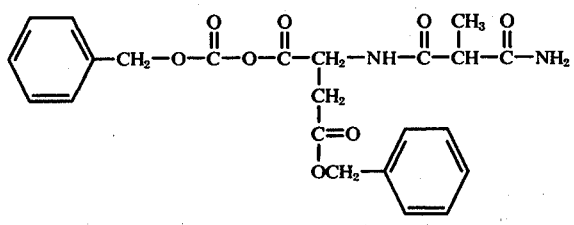

This compound may also be represented as:

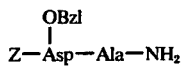

Z—Asp—Ala—NH$_2$

EXAMPLE 3

To a solution of 61.10 parts of β-benzyl N-benzyloxycarbonyl-L-aspartyl-D-alanine amide in 800 parts by volume of 75% acetic acid is added 6 parts of palladium black metal catalyst, and the resulting mixture is shaken with hydrogen at room temperature at atmospheric pressure for about 6.5 hours. The catalyst is removed by filtration, and the solvents removed by distillation under reduced pressure to obtain an oil. This oil is triturated with water and stripped under reduced pressure three times to afford a solid. The solid is then triturated with ethanol, filtered, and dried under vacuum to yield L-aspartyl-D-alanine amide monohydrate. This product is represented by the following structural formula.

H—Asp—Ala—NH$_2$ · H$_2$O  (L-D)

EXAMPLE 4

14.5 Parts of N-methylmorpholine is added to a stirred solution of 14.33 parts of L-aspartyl-D-alanine amide monohydrate in 189 parts of dimethylformamide and 12.6 parts by volume of a 5.60 N HCl/dioxane solution. Then, 33.2 parts of N-t-butoxycarbonyl-L-methionine 2,4,5-trichlorophenyl ester is added and the resulting mixture stirred for about 18 hours at room temperature. The solvent is removed in vacuo and the resultant syrupy oil dissolved in ethyl acetate. To this solution is added 0.82 parts of N,N-diethylaminoethylamine and the resulting mixture is stirred for about 35 minutes. The mixture is then washed twice with 5% potassium hydrogen sulfate solution, dried over anhydrous sodium sulfate, and stripped under reduced pressure to a gummy residue. The gum is triturated with ethyl ether, to yield crystals which are filtered and dried to afford N-t-butoxycarbonyl-L-methionyl-L-aspartyl-D-alanine amide. This product melts at about 107–110° C., and is represented by the following formula.

Boc—Met—Asp—Ala—NH$_2$  (L-L-D)

EXAMPLE 5

12.54 Parts of N-t-butoxycarbonyl-L-methionyl-L-aspartyl-D-alanine amide is dissolved in 107 parts by volume glacial acetic acid and 51.66 parts by volume of a 5.6 M solution of HCl/dioxane. The resultant mixture is stirred for 20 minutes and then stripped under reduced pressure to afford a solid. The solid is triturated with ethyl ether, cooled, and the resultant product washed with cold ethyl ether and vacuum dried. This solid is purified by countercurrent distribution to afford L-methionyl-L-aspartyl-D-alanine amide hydrochloride hydrated with 2/3 mole of water per mole, and represented by the following formula.

H-Met-Asp-Ala-NH$_2$ . HCl . 2/3H$_2$O  (L-L-D)

EXAMPLE 6

To a solution of 6.27 parts of L-methionyl-L-aspartyl-D-alanine amide hydrochloride hydrated with 2/3 mole of water per mole in 47 parts of dimethylformamide is added 7.91 parts of N-t-butoxycarbonyl-L-tryptophen 2,4,5-trichlorophenyl ester and 3.40 parts N-methylmorpholine. After stirring the resulting mixture overnight, the solvent is removed under high vacuum. The residue is dissolved in ethyl acetate. 0.181 Part by volume N,N-dimethylaminoethylamine is added and the mixture stirred for about 0.5 hour. The resultant mixture is washed three times with 5% potassium hydrogen sulfate, filtered, washed with saturated sodium chloride solution. Upon standing, a precipitate forms which is filtered to afford N-t-butoxycarbonyl-L-tryptophanyl-L-methionyl-L-aspartyl-D-alanine amide containing 1/3 mole of water of hydration per mole. This compound is represented by the following formula.

 . 1/3H$_2$O   

EXAMPLE 7

To a solution of N-t-butoxycarbonyl-L-tryptophanyl-L-methionyl-L-aspartyl-D-alanine amide hydrate in 11.6 parts by volume glacial acetic acid and 0.12 part by volume 2-mercaptoethanol is added 5.8 parts by volume of a 6.04 M solution of hydrochloric acid in dioxane. After stirring for approximately five minutes, the solvent is removed under reduced pressure. The residue is triturated with ethyl ether, filtered and vacuum-dried to afford L-tryptophanyl-L-methionyl-L-aspartyl-D-alanine amide hydrochloride. This compound is represented by the following formula.

 . HCl   

EXAMPLE 8

The substitution of an equivalent quantity of DL-2-aminoheptanoic acid in the procedure of Example 1 affords DL-2-aminoheptanamide, melting at 97°–101° C.

EXAMPLE 9

When an equivalent quantity of DL-2-aminoheptanamide is substituted for the D-alanine amide of Example 2, and the procedure detailed therein substantially repeated, there is obtained β-benzyl N-benzyloxycarbonyl-L-aspartyl-DL-2-aminoheptanamide. This compound melts at about 147°–150° C.

EXAMPLE 10

The reaction of β-benzyl N-benzyloxycarbonyl-L-aspartyl-DL-2-aminoheptanamide according to the procedure of Example 3 affords L-aspartyl-DL-2-aminoheptanamide, displaying an [α]$_D^{25}$ = +15° (concentration = 1.0 in acetic acid).

EXAMPLE 11

Repetition of the procedure of Example 4 using L-aspartyl-DL-2-aminoheptanamide in place of the L-aspartyl-D-alanine amide affords N-t-butoxycarbonyl-L-methionyl-L-aspartyl-DL-2-aminoheptanamide.

EXAMPLE 12

Substitution of an equivalent quantity of N-t-butoxycarbonyl-L-methionyl-L-aspartyl-DL-2-aminoheptanamide for the N-t-butoxycarbonyl-L-methionyl-L-aspartyl-D-alanine amide of Example 5 and substantial repetition of the procedure detailed therein affords L-methionyl-L-aspartyl-DL-2-aminoheptanamide hydrochloride.

EXAMPLE 13

When an equivalent quantity of L-methionyl-L-aspartyl-DL-2-aminoheptanamide hydrochloride is substituted for the L-methionyl-L-aspartyl-D-alanine amide hydrochloride of Example 6, and the procedure detailed therein substantially repeated, there is obtained N-t-butoxycarbonyl-L-tryptophanyl-L-methionyl-L-aspartyl-DL-2-aminoheptanamide. This compound melts at about 191°–193° C. with decomposition and is represented by the following formula.

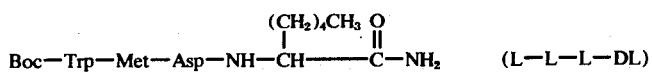

EXAMPLE 14

The reaction of N-t-butoxycarbonyl-L-tryptophanyl-L-methionyl-L-aspartyl-DL-2-aminoheptanamide according to the procedure of Example 7 affords L-tryptophanyl-L-methionyl-L-aspartyl-DL-2-aminoheptanamide hydrochloride. This compound is represented by the following formula.

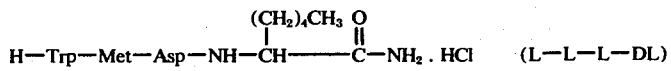

EXAMPLE 15

The substitution of an equivalent quantity of DL-2-amino-3-cyclopentylpropionic acid in the procedure of Example 1 affords DL-2-amino-3-cyclopentylpropionamide.

EXAMPLE 16

When an equivalent quantity of DL-2-amino-3-cyclopentylpropionamide is substituted for the D-alanine amide of Example 2, and the procedure detailed therein substantially repeated, there is obtained β-benzyl N-benzyloxycarbonyl-L-aspartyl-DL-2-amino-3-cyclopentylpropionamide, melting at about 172°–178° C.

EXAMPLE 17

The reaction of β-benzyl N-benzyloxycarbonyl-L-aspartyl-DL-2-amino-3-cyclopentylpropionamide according to the procedure of Example 3 affords L-aspartyl-DL-2-amino-3-cyclopentylpropionamide, melting at about 175°–190° C. with decomposition.

EXAMPLE 18

Repetition of the procedure of Example 4 using L-aspartyl-DL-2-amino-3-cyclopentylpropionamide in place of the L-aspartyl-D-alanine amide affords N-t-butoxycarbonyl-L-methionyl-L-aspartyl-DL-2-amino-3-cyclopentylpropionamide. This compound displays an [α]$_D^{25}$ = −42° (concentration = 1.0 in methanol).

EXAMPLE 19

Substitution of an equivalent quantity of N-t-butoxycarbonyl-L-methionyl-L-aspartyl-DL-2-amino-3-cyclopentylpropionamide for the N-t-butoxycarbonyl-L-methionyl-L-aspartyl-D-alanine amide of Example 5 and substantial repetition of the procedure detailed therein affords L-methionyl-L-aspartyl-DL-2-amino-3-cyclopentylpropionamide hydrochloride.

EXAMPLE 20

When an equivalent quantity of L-methionyl-L-aspartyl-DL-2-amino-3-cyclopentylpropionamide hydrochloride is substituted for the L-methionyl-L-aspartyl-D-alanine amide hydrochloride of Example 6, and the procedure detailed therein substantially repeated, there is obtained N-t-butoxycarbonyl-L-tryptophanyl-L-methionyl-L-aspartyl-DL-2-amino-3-cyclopentylpropionamide. This compound melts at about 207°–209° C. with decomposition and is represented by the following formula.

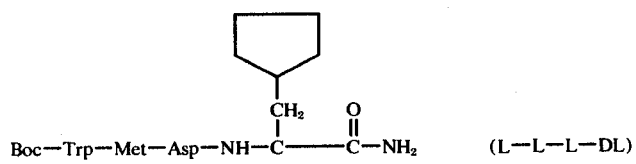

Boc—Trp—Met—Asp—NH—CH(CH₂-cyclopentyl)—C(=O)—NH₂    (L—L—L—DL)

EXAMPLE 21

The reaction of N-t-butoxycarbonyl-L-tryptophanyl-L-methionyl-L-aspartyl-DL-2-amino-3-cyclopentylpropionamide according to the procedure of Example 7 using trifluoroacetic acid instead of hydrochloric acid in dioxane affords L-tryptophanyl-L-methionyl-L-aspartyl-DL-2-amino-3-cyclopentylpropionamide trifluoracetate. This compound exhibits an $[\alpha]_D^{25} = -2°$ (concentration = 1.0 in acetic acid) and is represented by the following formula.

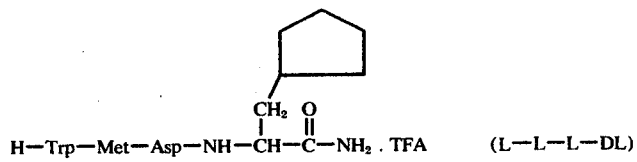

H—Trp—Met—Asp—NH—CH(CH₂-cyclopentyl)—C(=O)—NH₂ . TFA    (L—L—L—DL)

EXAMPLE 22

The substitution of an equivalent quantity of DL-2-amino-5-methylhexanoic acid in the procedure of Example 1 affords DL-2-amino-5-methylhexanamide.

EXAMPLE 23

When an equivalent quantity of DL-2-amino-5-methylhexanamide is substituted for the D-alanine amide of Example 2, and the procedure detailed therein substantially repeated, there is obtained β-benzyl N-benzyloxycarbonyl-L-aspartyl-DL-2-amino-5-methylhexanamide, melting at about 146°–149° C.

EXAMPLE 24

The reaction of β-benzyl N-benzyloxycarbonyl-L-aspartyl-DL-2-amino-5-methylhexanamide according to the procedure of Example 3 affords L-aspartyl-DL-2-amino-5-methylhexanamide, melting at about 215°–222° C.

EXAMPLE 25

Repetition of the procedure of Example 4 using L-aspartyl-DL-2-amino-5-methylhexanamide in place of the L-aspartyl-D-alanine amide affords N-t-butoxycarbonyl-L-methionyl-L-aspartyl-DL-2-amino-5-methylhexanamide.

EXAMPLE 26

Substitution of an equivalent quantity of N-t-butoxycarbonyl-L-methionyl-L-aspartyl-DL-2-amino-5-methylhexanamide for the N-t-butoxycarbonyl-L-methionyl-L-aspartyl-D-alanine amide of Example 5 and substantial repetition of the procedure detailed therein affords L-methionyl-L-aspartyl-DL-2-amino-5-methylhexanamide hydrochloride.

EXAMPLE 27

When an equivalent quantity of L-methionyl-L-aspartyl-DL-2-amino-5-methylhexanamide hydrochloride is substituted for the L-methionyl-L-aspartyl-D-alanine amide hydrochloride of Example 6, and the procedure detailed therein substantially repeated, there is obtained N-t-butoxycarbonyl-L-tryptophanyl-L-methionyl-L-aspartyl-DL-2-amino-5-methylhexanamide. This compound melts at about 150°–157° C. and is represented by the following formula.

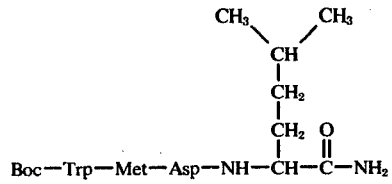

Boc—Trp—Met—Asp—NH—CH(CH₂CH₂CH(CH₃)₂)—C(=O)—NH₂    (L—L—L—DL)

EXAMPLE 28

The reaction of N-t-butoxycarbonyl-L-tryptophanyl-L-methionyl-L-aspartyl-DL-2-amino-5-methylhexanamide according to the procedure of Example 7 using trifluoroacetic acid instead of hydrochloric acid in dioxane affords L-tryptophanyl-L-methionyl-L-aspartyl-DL-2-amino-5-methylhexanamide trifluoroacetate. This compound exhibits an $[\alpha]_D^{25} = -8°$ (concentration = 1.0 in methanol) and is represented by the following formula.

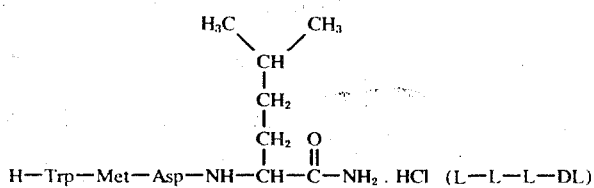

H—Trp—Met—Asp—NH—CH—C—NH$_2$ . HCl  (L—L—L—DL)

EXAMPLE 29

The substitution of an equivalent quantity of DL-norleucine in the procedure of Example 1 affords DL-norleucine amide.

EXAMPLE 30

When an equivalent quantity of DL-norleucine amide is substituted for the D-alanine amide of Example 2, and the procedure detailed therein substantially repeated, there is obtained β-benzyl N-benzyloxycarbonyl-L-aspartyl-DL-norleucine amide.

EXAMPLE 31

The reaction of β-benzyl N-benzyloxycarbonyl-L-aspartyl-DL-norleucine amide according to the procedure of Example 3 affords L-aspartyl-DL-norleucine amide. This compound exhibits an $[\alpha]_D^{25} = +29°$ (concentration = 1.0 in acetic acid).

EXAMPLE 32

Repetition of the procedure of Example 4 using L-aspartyl-DL-norleucine amide in place of the L-aspartyl-D-alanine amide affords N-t-butoxycarbonyl-L-methionyl-L-aspartyl-DL-norleucine amide, melting at about 204°-205° C.

EXAMPLE 33

Substitution of an equivalent quantity of N-t-butoxycarbonyl-L-methionyl-L-aspartyl-DL-norleucine amide for the N-t-butoxycarbonyl-L-methionyl-L-aspartyl-D-alanine amide of Example 5 and substantial repetition of the procedure detailed therein affords L-methionyl-L-aspartyl-DL-norleucine amide hydrochloride. This compound exhibits an $[\alpha]_D^{25} = +15°$ (concentration = 1.0 in acetic acid.

EXAMPLE 34

When an equivalent quantity of L-methionyl-L-aspartyl-DL-norleucine amide hydrochloride is substituted for the L-methionyl-L-aspartyl-D-alanine amide hydrochloride of Example 6, and the procedure detailed therein substantially repeated, there is obtained N-t-butoxycarbonyl-L-tryptophanyl-methionyl-L-aspartyl-DL-norleucine amide. This compound displays an $[\alpha]_D^{25} = -31°$ (concentration = 1.0 in methanol) and is represented by the following formula.

Boc-Trp-Met-Asp-Nle-NH$_2$ (L-L-L-DL)

EXAMPLE 35

The reaction of N-t-butoxycarbonyl-L-tryptophanyl-L-methionyl-L-aspartyl-DL-norleucine amide according to the procedure of Example 7 using trifluoroacetic acid instead of hydrochloric acid in dioxane affords L-tryptophanyl-L-methionyl-L-aspartyl-DL-norleucine amide trifluoroacetate. This compound is represented by the following formula.

H-Trp-Met-Asp-Nle-NH$_2$ . TFA (L-L-L-DL)

This compound exhibits an $[\alpha]_D^{25} = -18°$ (concentration = 1.0 in methanol).

EXAMPLE 36

The substitution of an equivalent quantity of 2-amino-2-methylpropionic acid in the procedure of Example 1 affords 2-amino-2-methylpropionamide.

EXAMPLE 37

When an equivalent quantity of 2-amino-2-methylpropionamide is substituted for the D-alanine amide of Example 2, and the procedure detailed therein substantially repeated, there is obtained β-benzyl N-benzyloxycarbonyl-L-aspartyl-2-amino-2-methylpropionamide, melting at about 107°-108° C.

EXAMPLE 38

The reaction of β-benzyl-N-benzyloxycarbonyl-L-aspartyl-2-amino-2-methylpropionamide according to the procedure of Example 3 affords L-aspartyl-2-amino-2-methylpropionamide.

EXAMPLE 39

Repetition of the procedure of Example 4 using L-aspartyl-2-amino-2-methylpropionamide in place of the L-aspartyl-D-alanine amide affords N-t-butoxycarbonyl-L-methionyl-L-aspartyl-2-amino-2-methylpropionamide. Elemental analysis of this compound shows C: 48.33%; H: 7.31%; N: 12.16% and S: 7.19%. Theory is C: 48.20%; H: 7.19%; N: 12.49% and S: 7.15%.

EXAMPLE 40

Substitution of an equivalent quantity of N-t-butoxycarbonyl-L-methionyl-L-aspartyl-2-amino-2-methylpropionamide for the N-t-butoxycarbonyl-L-methionyl-L-aspartyl-D-alanine amide of Example 5 and substantial repetition of the procedure detailed therein affords L-methionyl-L-aspartyl-2-amino-2-methylpropionamide hydrochloride. Elemental analysis of this compound shows C: 40.59%; H: 6.75%; N: 14.17%; S: 8.36% and Cl: 8.88%. Theory is C: 40.57%; H: 6.55%; N: 14.56%; S: 8.33% and Cl: 9.21%.

EXAMPLE 41

When an equivalent quantity of L-methionyl-L-aspartyl-2-amino-2-methylpropionamide hydrochloride is substituted for the L-methionyl-L-aspartyl-D-alanine amide hydrochloride of Example 6, and the procedure detailed therein substantially repeated, there is obtained N-t-butoxycarbonyl-L-tryptophanyl-L-methionyl-L-aspartyl-2-amino-2-methylpropionamide containing ⅓ mole of water of hydration per mole. This compound is represented by the following formula.

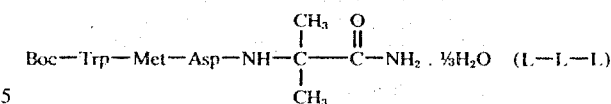

Elemental analysis of this compound shows C: 54.45%; H: 6.69%; N: 12.69% and S: 4.96%. Theory is C: 54.36%; H: 6.71%; N: 13.11% and S: 5.00%.

EXAMPLE 42

The reaction of N-t-butoxycarbonyl-L-tryptophanyl-L-methionyl-L-aspartyl-2-amino-2-methylpropionamide according to the procedure of Example 7 affords L-tryptophanyl-L-methionyl-L-aspartyl-2-amino-2-methylpropionamide hydrochloride containing ⅓ mole of water of hydration per mole. This compound is represented by the following formula.

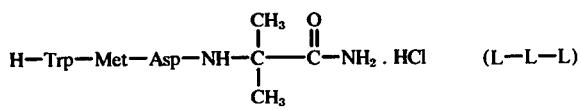

Elemental analysis of this compound shows C: 49.84%; H: 6.53%; N: 12.93%; S: 5.32% and Cl: 6.07%. Theory is C: 49.95%; H: 6.23%; N: 14.56%; S: 5.56% and Cl: 6.14%.

EXAMPLE 43

The substitution of an equivalent quantity of DL-2-aminobutanoic acid in the procedure of Example 1 affords DL-2-aminobutanamide.

EXAMPLE 44

When an equivalent quantity of DL-2-aminobutanamide is substituted for the D-alanine amide of Example 2, and the procedure detailed therein substantially repeated, there is obtained β-benzyl N-benzyloxycarbonyl-L-aspartyl-DL-2-aminobutanamide.

EXAMPLE 45

The reaction of β-benzyl N-benzyloxycarbonyl-L-aspartyl-DL-2-aminobutanamide according to the procedure of Example 3 affords L-aspartyl-DL-2-aminobutanamide.

EXAMPLE 46

Repetition of the procedure of Example 4 using L-aspartyl-DL-2-aminobutanamide in place of the L-aspartyl-D-alanine amide affords N-t-butoxycarbonyl-L-methionyl-L-aspartyl-DL-2-aminobutanamide.

EXAMPLE 47

Substitution of an equivalent quantity of N-t-butoxycarbonyl-L-methionyl-L-aspartyl-DL-2-aminobutanamide for the N-t-butoxycarbonyl-L-methionyl-L-aspartyl-D-alanine amide of Example 5 and substantial repetition of the procedure detailed therein affords L-methionyl-L-aspartyl-DL-2-aminobutanamide hydrochloride.

EXAMPLE 48

When an equivalent quantity of L-methionyl-L-aspartyl-DL-2-aminobutanamide hydrochloride is substituted for the L-methionyl-L-aspartyl-D-alanine amide hydrochloride of Example 6, and the procedure detailed therein substantially repeated, there is obtained N-t-butoxycarbonyl-L-tryptophanyl-L-methionyl-L-aspartyl-DL-2-aminobutanamide. This compound is represented by the following formula.

Boc-Trp-Met-Asp-Abu-NH₂      (L-L-L-DL)

EXAMPLE 49

The reaction of N-t-butoxycarbonyl-L-tryptophanyl-L-methionyl-L-aspartyl-DL-2-aminobutanamide according to the procedure of Example 7 affords L-tryptophanyl-L-methionyl-L-aspartyl-DL-2-aminobutanamide hydrochloride. This compound is represented by the following formula.

H-Trp-Met-Asp-Abu-NH₂ · HCl      (L-L-L-DL)

EXAMPLE 50

The substitution of an equivalent quantity of D-valine in the procedure of Example 1 affords D-valine amide.

EXAMPLE 51

When an equivalent quantity of D-valine amide is substituted for the D-alanine amide of Example 2, and the procedure detailed therein substantially repeated, there is obtained β-benzyl N-benzyloxycarbonyl-L-aspartyl-D-valine amide.

EXAMPLE 52

The reaction of β-benzyl N-benzyloxycarbonyl-L-aspartyl-D-valine amide according to the procedure of Example 3 affords L-aspartyl-D-valine amide.

EXAMPLE 53

Repetition of the procedure of Example 4 using L-aspartyl-D-valine amide in place of the L-aspartyl-D-alanine amide affords N-t-butoxycarbonyl-L-methionyl-L-aspartyl-D-valine amide.

EXAMPLE 54

Substitution of an equivalent quantity of N-t-butoxycarbonyl-L-methionyl-L-aspartyl-D-valine amide for the N-t-butoxycarbonyl-L-methionyl-L-aspartyl-D-alanine amide of Example 5 and substantial repetition of the procedure detailed therein affords L-methionyl-L-aspartyl-D-valine amide hydrochloride.

EXAMPLE 55

When an equivalent quantity of L-methionyl-L-aspartyl-D-valine amide hydrochloride is substituted for the L-methionyl-L-aspartyl-D-alanine amide hydrochloride of Example 6, and the procedure detailed therein substantially repeated, there is obtained N-t-butoxycarbonyl-L-tryptophanyl-L-methionyl-L-aspartyl-D-valine amide. This compound is represented by the following formula.

Boc-Trp-Met-Asp-Val-NH₂      (L-L-L-D)

EXAMPLE 56

The reaction of N-t-butoxycarbonyl-L-tryptophanyl-L-methionyl-L-aspartyl-D-valine amide according to the procedure of Example 7 affords L-tryptophanyl-L-methionyl-L-aspartyl-D-valine amide hydrochloride. This compound is represented by the following formula.

H-Trp-Met-Asp-Val-NH₂ · HCl      (L-L-L-D)

EXAMPLE 57

The substitution of an equivalent quantity of DL-norvaline in the procedure of Example 1 affords DL-norvaline amide.

EXAMPLE 58

When an equivalent quantity of DL-norvaline amide is substituted for the D-alanine amide of Example 2, and the procedure detailed therein substantially repeated, there is obtained β-benzyl N-benzyloxycarbonyl-L-aspartyl-DL-norvaline amide.

EXAMPLE 59

The reaction of β-benzyl N-benzyloxycarbonyl-L-aspartyl-DL-norvaline amide according to the procedure of Example 3 affords L-aspartyl-DL-norvaline amide.

EXAMPLE 60

Repetition of the procedure of Example 4 using L-aspartyl-DL-norvaline amide in place of the L-aspartyl-D-alanine amide affords N-t-butoxycarbonyl-L-methionyl-L-aspartyl-DL-norvaline amide.

EXAMPLE 61

Substitution of an equivalent quantity of N-t-butoxycarbonyl-L-methionyl-L-aspartyl-DL-norvaline amide for the N-t-butoxycarbonyl-L-methionyl-L-aspartyl-D-alanine amide of Example 5 and substantial repetition of the procedure detailed therein affords L-methionyl-L-aspartyl-DL-norvaline amide hydrochloride.

EXAMPLE 62

When equivalent quantities of L-methionyl-L-aspartyl-DL-norvaline amide hydrochloride and N-benzyloxycarbonyl-L-tryptophan 2,4,5-trichlorophenyl ester are substituted for the L-methionyl-L-aspartyl-D-alanine amide hydrochloride and the N-t-butoxycarbonyl-L-tryptophan 2,4,5-trichlorophenyl ester of Example 6, and the procedure detailed therein substantially repeated, there is obtained N-benzyloxycarbonyl-L-tryptophanyl-L-methionyl-L-aspartyl-DL-norvaline amide. This compound is represented by the following formula.

Z-Trp-Met-Asp-Nva-NH₂      (L-L-L-DL)

EXAMPLE 63

N-benzyloxycarbonyl-L-tryptophanyl-L-methionyl-L-aspartyl-DL-norvaline amide is dissolved in 10 parts glacial acetic acid containing 2 parts methylethyl sulfide. Then, 10 parts of 6 M hydrobromic acid in acetic acid is added and the solution is allowed to stand for one hour at room temperature. The solvents are removed under vacuum below 40° C. and the residue shaken with ether to afford L-tryptophanyl-L-methionyl-L-aspartyl-DL-norvaline amide hydrobromide. This compound is represented by the following formula.

H-Trp-Met-Asp-Leu-NH₂ · HBr      (L-L-L-DL)

EXAMPLE 64

The substitution of an equivalent quantity of D-leucine in the procedure of Example 1 affords D-leucine amide.

EXAMPLE 65

When an equivalent quantity of D-leucine amide is substituted for the D-alanine amide of Example 2, and the procedure detailed therein substantially repeated, there is obtained β-benzyl N-benzyloxycarbonyl-L-aspartyl-D-leucine amide.

EXAMPLE 66

The reaction of β-benzyloxycarbonyl-L-aspartyl-D-leucine amide according to the procedure of Example 3 affords L-aspartyl-D-leucine amide.

EXAMPLE 67

Repetition of the procedure of Example 4 using L-aspartyl-D-leucine amide in place of the L-aspartyl-D-alanine amide affords N-t-butoxycarbonyl-L-methionyl-L-aspartyl-D-leucine amide.

EXAMPLE 68

Substitution of an equivalent quantity of N-t-butoxycarbonyl-L-methionyl-L-aspartyl-D-leucine amide for the N-t-butoxycarbonyl-L-methionyl-L-aspartyl-D-alanine amide of Example 5 and substantial repetition of the procedure detailed therein affords L-methionyl-L-aspartyl-D-leucine amide hydrochloride.

EXAMPLE 69

When an equivalent quantity of L-methionyl-L-aspartyl-D-leucine amide hydrochloride is substituted for the L-methionyl-L-aspartyl-D-alanine amide hydrochloride of Example 6, and the procedure detailed therein substantially repeated, there is obtained N-t-butoxycarbonyl-L-tryptophanyl-L-methionyl-L-aspartyl-D-leucine amide. This compound is represented by the following formula.

Boc-Trp-Met-Asp-Leu-NH₂      (L-L-L-D)

EXAMPLE 70

The reaction of N-t-butoxycarbonyl-L-tryptophanyl-L-methionyl-L-aspartyl-D-leucine amide according to the procedure of Example 7 affords L-tryptophanyl-L-methionyl-L-aspartyl-D-leucine amide hydrochloride. This compound is represented by the following formula.

H-Trp-Met-Asp-Leu-NH₂ · HCl      (L-L-L-D)

EXAMPLE 71

To a solution of 44.64 parts of benzyloxycarbonyl-D-alanine in 276 parts of tetrahydrofuran is added 2.02 parts of N-methylmorpholine. The resulting solution is cooled to about −30° C. and 25.4 parts of isobutyl chloroformate is added with stirring. After stirring for about 5 minutes, 13.0 parts of n-propylamine is added and the mixture stirred for a further 10 minutes. The mixture is cooled overnight and then concentrated under reduced pressure to a syrup. This residue is dissolved in methylene chloride and washed successively with 2 M potassium carbonate, water, twice with 1 M hydrochloric acid and finally, twice with water. After drying over anhydrous magnesium sulfate the solution is concentrated under reduced pressure. The residue is diluted with 180 parts of ethyl ether and cooled to 5° C. The resulting crystals are filtered, washed with ether and dried to give benzyloxycarbonyl-D-alanine n-propylamide, melting at about 116.5°–120° C.

35.0 Parts of benzyloxycarbonyl-D-alanine n-propylamide is dissolved in ethanol. Then, palladium black catalyst is added and the mixture is shaken at about 60 psi at room temperature for several hours or until one molecular equivalent of hydrogen has been absorbed. The catalyst is removed by filtration, and the resulting solution is decolorized with charcoal. Removal of the solvents under reduced pressure affords, as an oil, D-alanine n-propylamide.

EXAMPLE 72

When an equivalent quantity of D-alanine n-propylamide is substituted for the D-alanine amide of Example 2, and the procedure detailed therein substantially repeated, there is obtained β-benzyl N-benzyloxycarbonyl-L-aspartyl-D-alanine n-propylamide, melting at about 169°–171° C.

EXAMPLE 73

The reaction of β-benzyl N-benzyloxycarbonyl-L-aspartyl-D-alanine n-propylamide according to the procedure of Example 3 affords L-aspartyl-D-alanine n-propylamide, melting at 198°–199° C., with decomposition.

EXAMPLE 74

Repetition of the procedure of Example 4 using L-aspartyl-D-alanine n-propylamide in place of the L-aspartyl-D-alanine amide affords N-t-butoxycarbonyl-L-methionyl-L-aspartyl-D-alanine n-propylamide, melting at about 172.5°–173° C.

EXAMPLE 75

Substitution of an equivalent quantity of N-t-butoxycarbonyl-L-methionyl-L-aspartyl-D-alanine n-propylamide for the N-t-butoxycarbonyl-L-methionyl-L-aspartyl-D-alanine amide of Example 5 and substantial repetition of the procedure detailed therein affords L-methionyl-L-aspartyl-D-alanine n-propylamide hydrochloride. Actual elemental analysis of this compound shows C: 43.34%; H: 7.04%; N: 13.34%; S: 7.88% and Cl: 8.95%. Theoretical analysis for this compound is C: 43.63%; H: 7.08%; N: 13.57%; S: 7.77% and Cl: 8.59%.

EXAMPLE 76

When an equivalent quantity of L-methionyl-L-aspartyl-D-alanine n-propylamide hydrochloride is substituted for the L-methionyl-L-aspartyl-D-alanine amide hydrochloride of Example 6, and the procedure detailed therein substantially repeated, there is obtained N-t-butoxycarbonyl-L-tryptophanyl-L-methionyl-L-aspartyl-D-alanine n-propylamide. This compound melts at about 143.5°–148° C. with decomposition and is represented by the following formula.

Boc-Trp-Met-Asp-Ala-NH-CH₂CH₂CH₃     (L-L-L-D)

EXAMPLE 77

The reaction of N-t-butoxycarbonyl-L-tryptophanyl-L-methionyl-L-aspartyl-D-alanine n-propylamide according to the procedure of Example 7 affords L-tryptophanyl-L-methionyl-L-aspartyl-D-alanine n-propylamide hydrochloride. This compound is represented by the following formula.

H-Trp-Met-Asp-Ala-NH-CH₂CH₂CH₃ · HCl     (L-L-L-D)

EXAMPLE 78

36.9 Parts of methyl 2-amino-2-methylpropionate hydrochloride is shaken with 53.0 parts by volume of a 5 M potassium carbonate solution. The resulting mixture is extracted three times with portions of methylene chloride. The methylene chloride extracts are combined, dried over anhydrous magnesium sulfate and stripped under reduced pressure to afford methyl 2-amino-2-methylpropionate.

To a solution of 26.3 parts of methyl 2-amino-2-methylpropionate in methanol is added 70 parts of n-propylamine. The mixture is placed in a bomb and left at a temperature of 100° C. for one week. The solvents are then stripped off under reduced pressure. Distillation of the residual oil affords N¹-propyl-2-amino-2-methylpropionamide, boiling at 58° C. at 0.1 mm pressure.

EXAMPLE 79

When an equivalent quantity of N¹-propyl-2-amino-2-methylpropionamide is substituted for the D-alanine amide of Example 2, and the procedure detailed therein substantially repeated, there is obtained β-benzyl N-benzyloxycarbonyl-L-aspartyl-N¹-propyl-2-amino-2-methylpropionamide hydrated with 1⅓ moles of water per mole. Actual elemental analysis of this compound shows C: 61.48%; H: 6.60% and N: 8.23%. Theoretical elemental analysis is C: 61.52%; H: 7.08% and N: 8.28%.

EXAMPLE 80

The reaction of β-benzyl N-benzyloxycarbonyl-L-aspartyl-N¹-propyl-2-amino-2-methylpropionamide hydrate according to the procedure of Example 3 affords L-aspartyl-N¹-propyl-2-amino-2-methylpropionamide.

EXAMPLE 81

Repetition of the procedure of Example 4 using L-aspartyl-N¹-propyl-2-amino-2-methylpropionamide in place of the L-aspartyl-D-alanine amide affords N-t-butoxycarbonyl-L-methionyl-L-aspartyl-N¹-propyl-2-amino-2-methylpropionamide hydrated with ⅓ mole of water per mole. Actual elemental analysis of this compound shows C: 50.67%; H: 7.77%; N: 11.07% and S: 6.37%. Theoretical elemental analysis is C: 50.78%; H: 7.85%; N: 11.28% and S: 6.46%.

EXAMPLE 82

Substitution of an equivalent quantity of N-t-butoxycarbonyl-L-methionyl-L-aspartyl-N¹-propyl-2-amino-2-methylpropionamide hydrate for the N-t-butoxycarbonyl-L-methionyl-L-aspartyl-D-alanine amide of Example 5 and substantial repetition of the procedure detailed therein affords L-methionyl-L-aspartyl-N¹-propyl-2-amino-2-methylpropionamide hydrochloride containing ⅓ mole of water of hydration per mole.

Actual elemental analysis of this compound shows C: 44.45%; H: 7.45%; N: 12.38%; S: 7.20% and Cl: 8.04%. Theoretical elemental analysis is C: 44.38%; H: 7.37%; N: 12.94%; S: 7.41% and Cl: 8.19%.

EXAMPLE 83

When an equivalent quantity of L-methionyl-L-aspartyl-N$^1$-propyl-2-amino-2-methylpropionamide hydrochloride hydrate is substituted for the L-methionyl-L-aspartyl-D-alanine amide hydrochloride of Example 6, and the procedure detailed therein substantially repeated, there is obtained N-t-butoxycarbonyl-L-tryptophanyl-L-methionyl-L-aspartyl-N$^1$-propyl-2-amino-2-methylpropionamide hydrated with 2/3 mole of water per mole. Actual elemental analysis shows C: 55.82%; H: 7.21%; N: 12.37% and S: 4.72%. Theoretical elemental analysis is C: 55.79%; H: 7.22%; N: 12.20% and S: 4.66%. This compound is represented by the following formula.

$$\text{Boc—Trp—Met—Asp—NH}-\underset{\underset{CH_3}{|}}{\overset{\overset{CH_3}{|}}{C}}-\overset{O}{\overset{\|}{C}}-\text{NH—CH}_2\text{CH}_2\text{CH}_3 \cdot \tfrac{2}{3}\text{H}_2\text{O} \qquad (L\text{—}L\text{—}L)$$

EXAMPLE 84

The reaction of N-t-butoxycarbonyl-L-tryptophanyl-L-methionyl-L-aspartyl-N$^1$-propyl-2-amino-2-methylpropionamide hydrate according to the procedure of Example 7 affords L-tryptophanyl-L-methionyl-L-aspartyl-N$^1$-propyl-2-amino-2-methylpropionamide hydrochloride hemihydrate. This compound is represented by the following formula.

$$\text{H—Trp—Met—Asp—NH}-\underset{\underset{CH_3}{|}}{\overset{\overset{CH_3}{|}}{C}}-\overset{O}{\overset{\|}{C}}-\text{NH—CH}_2\text{CH}_2\text{CH}_3 \cdot \text{HCl} \cdot \tfrac{1}{2}\text{H}_2\text{O} \qquad (L\text{—}L\text{—}L)$$

Actual elemental analysis of this compound shows C: 51.36%; H: 6.79%; N: 13.36%; S: 5.33% and Cl: 5.56%. Theoretical elemental analysis is C: 51.35%; H: 6.63%; N: 13.82%; S: 5.27% and Cl: 5.83%.

What is claimed is:

1. A compound of the formula $$\text{A-Trp-Met-Asp-Y-NHR} \qquad \text{I}$$

wherein
A is hydrogen, alkanoyl containing 2 to 6 carbon atoms, succinyl, t-butoxycarbonyl, benzyloxycarbonyl, D-pyroglutamyl or L-pyroglutamyl;
Y is a radical of the formula $$-\text{HN}-\underset{\underset{R'}{|}}{\text{CH}}-\overset{O}{\overset{\|}{C}}-$$

wherein
R' is an alkyl radical containing 1 to 6 carbon atoms or a methylcyclopentyl radical and the stereochemical configuration is D, or DL, or Y is a radical of the formula $$-\text{NH}-\underset{\underset{CH_3}{|}}{\overset{\overset{CH_3}{|}}{C}}-\overset{O}{\overset{\|}{C}}-$$

R is hydrogen or an alkyl radical containing 1 to 6 carbon atoms; and pharmaceutically acceptable acid addition salts thereof; and the optically active amino acid Trp, Met and Asp residues are of the L-configuration.

2. A compound according to claim 1 of the formula $$\text{A—Trp—Met—Asp—HN}-\underset{\underset{CH_3}{|}}{\overset{\overset{CH_3}{|}}{C}}-\overset{O}{\overset{\|}{C}}-\text{NHR}$$

wherein
A is hydrogen, alkanoyl containing 2 to 6 carbon atoms, succinyl, t-butoxycarbonyl, benzyloxycarbonyl, D-pyroglutamyl or L-pyroglutamyl;
R is hydrogen or an alkyl radical containing 1 to 6 carbon atoms; and pharmaceutically acceptable acid addition salts thereof; and the optically active amino acid Trp, Met and Asp residues are of the L-configuration.

3. The compound according to claim 1 which is N-t-butoxycarbonyl-L-tryptophanyl-L-methionyl-L-aspartyl-N$^1$-propyl-2-amino-2-methylpropionamide.

4. A compound according to claim 1 of the formula $$\text{A—Trp—Met—Asp—HN}-\underset{\underset{R'}{|}}{\text{CH}}-\overset{O}{\overset{\|}{C}}-\text{NHR}$$

wherein
A is hydrogen, alkanoyl containing 2 to 6 carbon atoms, succinyl, t-butoxycarbonyl, benzyloxycarbonyl, D-pyroglutamyl or L-pyroglutamyl;
R' is an alkyl radical containing 1 to 6 carbon atoms or a methylcyclopentyl radical;
R is hydrogen or an alkyl radical containing 1 to 6 carbon atoms; and pharmaceutically acceptable acid addition salts thereof, with the stereochemical configuration being L-L-L-D.

5. The compound according to Claim 1 which is L-tryptophanyl-L-methionyl-L-aspartyl-D-alanine n-propylamide hydrochloride hemihydrate.

6. The compound according to claim 1 which is N-t-butoxycarbonyl-L-tryptophanyl-L-methionyl-L-aspartyl-D-alanine n-propylamide.

7. The compound according to claim 1 which is N-t-butoxycarbonyl-L-tryptophanyl-L-methionyl-L-aspartyl-DL-2-aminoheptanamide.

8. The compound according to claim 1 which is N-t-butoxycarbonyl-L-tryptophanyl-L-methionyl-L-aspartyl-DL-2-amino-3-cyclopentylpropionamide.

9. The compound according to claim 1 which is N-t-butoxycarbonyl-L-tryptophanyl-L-methionyl-L-aspartyl-DL-2-amino-5-methylhexanamide.

10. The compound according to claim 1 which is N-t-butoxycarbonyl-L-tryptophanyl-L-methionyl-L-aspartyl-DL-norleucine amide.

11. The compound according to claim 1 which is N-t-butoxycarbonyl-L-tryptophanyl-L-methionyl-L-aspartyl-D-alanine amide.

* * * * *